United States Patent [19]

Francis

[11] Patent Number: 4,659,699

[45] Date of Patent: Apr. 21, 1987

[54] PROCESS FOR FREEZE DRYING CYCLOPHOSPHAMIDE

[75] Inventor: Daniel L. Francis, Ravenna, Ohio

[73] Assignee: Cetus-Ben Venue Therapeutics, Emeryville, Calif.

[21] Appl. No.: 612,626

[22] Filed: May 21, 1984

Related U.S. Application Data

[63] Continuation-in-part of Ser. No. 524,899, Aug. 22, 1983, abandoned.

[51] Int. Cl.$^4$ .......................... A61K 31/70; C07H 1/00
[52] U.S. Cl. .......................................... 514/53; 514/23; 514/54; 514/960; 536/124; 536/127; 536/18.2; 536/55.3; 536/117; 536/17.1
[58] Field of Search ...................... 536/17.1, 124, 127, 536/55.3, 27, 18.2; 514/23, 110, 53, 54, 960

[56] References Cited

U.S. PATENT DOCUMENTS

| | | | |
|---|---|---|---|
| 3,018,302 | 1/1962 | Arnold et al. | 260/984 |
| 3,356,652 | 12/1967 | Ray-Chaudhuri | 536/18.2 |
| 4,157,440 | 6/1979 | Reiner et al. | 536/27 |
| 4,404,368 | 9/1983 | Alvardo-Urbina et al. | 536/27 |
| 4,537,883 | 8/1985 | Alexander et al. | 514/110 |

FOREIGN PATENT DOCUMENTS 1951822 4/1971 Fed. Rep. of Germany ...... 514/110

Primary Examiner—Johnnie R. Brown
Attorney, Agent, or Firm—Albert P. Halluin; Janet E. Hasak

[57] ABSTRACT

A two-stage process for freeze-drying an aqueous solution of a dosage amount of cyclophosphamide to yield a hydrate of cyclophosphamide (referred to as "CPA" for brevity), comprises, in a first stage, freeze-drying a solution of CPA in combination with an excipient until the moisture content of the freeze-dried material is less than 2% by wt, based on the amount of anhydrous CPA present; and, in a second stage, rehydrating the freeze-dried material until the moisture content of the product is in the critical range of from about 2% to 7% by wt, based on the net wt of CPA product, it being essential for stability of the product that at least one sugar excipient be present. The process requires that a major amount by weight of the excipient(s) or all of it, be mannitol, optionally with an additional sugar and/or a carboxylic acid, and/or a buffer salt; and, the mannitol is present in an amount at least one-half (0.5 times) as mush as the CPA (anhyd) present. To produce a dosage form of a 'plug' or 'cake' which is free of flakes and granules, or bubbles on its surface, and/or voids within the product (or "plug"), any of which are individually no greater than 2 mm in equivalent diameter ("equiv. dia."), requires a unique combination of carefully controlled process steps. The preferred CPA product obtained by the process provides a dosage amount of stable freeze-dried and rehydrated CPA as a hydrate which includes at least an equivalent amount by weight, and up to 5 times as much, of mannitol. The dosage amount may include sodium chloride to adjust tonicity, and a buffer salt to maintain pH.

21 Claims, No Drawings

PROCESS FOR FREEZE DRYING CYCLOPHOSPHAMIDE

CROSS-REFERENCE TO RELATED APPLICATION

This is a continuation-in-part of Ser. No. 524,899 filed Aug. 22, 1983, now abandoned.

BACKGROUND OF THE INVENTION

Pharmaceuticals, biological specimens and foodstuffs are among the most commonly freeze-dried ("lyophilized") materials. Though it would seem relatively easy to achieve desirable results, namely the dry state, by starting with an aqueous solution of a pharmaceutical, then freezing the solution and subliming the resulting ice, it is not. The purpose of freeze-drying is to minimize the changes in the properties of the substance while improving its stability at or near room temperature. Much has been published as to how to do this effectively (See, for example, *Edwards Freeze-Drying Handbook*, by Terence W. G. Rowe and John W. Snowman, published by Edwards High Vacuum, Crawley, England (1976). The problem is that in one or the other stages of freeze-drying, the material being freeze dried is undesirably altered.

A great deal of well-publicized effort has been directed to the freeze-drying of biological materials because of the criticality of the process steps required to obtain satisfactory results (see *Freezing and Drying of Biological Materials*, edited by O. St. Whitelock, "Annals of the New York Academy of Sciences", Vol 85, Art. 2, pgs 501–734, published by The Academy 1960). A comparable amount of less well-publicized effort has been directed to the freeze-drying of various pharmaceuticals for the twin purposes of maintaining their potency and stability over extended periods of time under ambient conditions, and to provide convenience in dispensing or using the pharmaceuticals.

Much attention has been paid, and much effort had been directed, neither too well-publicized, to the importance of presenting a pharmaceutically elegant dosage quantity of a pharmaceutical which must also maintain its potency and stability. In most instances, the freeze-dried pharmaceutical is deposited as a product (or "cake") which adheres to the sides of the vial or other container in which the precursor solution is freeze-dried. As the preferred form of packaging freeze-dried pharmaceuticals is in glass vials or containers, it will immediately be evident that a cake or plug tightly held in a glass container, near its bottom, has greater visual appeal than a loose powder, particularly if the powder has a proclivity to dust. When a pharmaceutical defies being successfully freeze-dried, that is, being reduced to a stable pharmaceutically elegant product without deleteriously affecting the physiological properties of the pharmaceutical, it is generally packaged as a dry powder.

This is precisely the packaging history of cyclophosphamide monohydrate and cyclophosphamide (either of which is referred to herein as "CPA" for brevity), which is a synthetic antineoplastic drug and immunosuppressive agent widely used for the treatment of a variety of malignant and non-malignant diseases. CPA is described in greater detail in U.S. Pat. No. 3,018,302 which is incorporated by reference thereto as if fully set forth herein, and also in the Merck Index, inter alia, the disclosures of which are similarly incorporated by reference.

The drug is currently packaged as a "dry" powder in vials into which dosage amounts of CPA in combination with sodium chloride are "powder filled". By "powder filled" I refer to the drug being measured into the vials in predetermined amounts as a mixture of powders. The water content of the powder in a dosage amount of powder filled CPA is in the range from 4.3–4.8 percent by weight (% by wt) based on the total weight of the powder in the vial. Just prior to use, the powder in the vials is reconstituted with Sterile Water for Injection, USP, or other suitable sterile solvents or diluents, and the reconstituted solution is administered to a patient.

However, the dissolution in water may not be readily accomplished, the time of solution for a 0.5 g dosage amount (which contains about 0.225 g NaCl solids) ranging from about 2 min (minutes) to about 2 hr (hours) or more, depending upon the particular physical/chemical characteristics of the CPA and NaCl in a particular batch of powder measured into a vial. A freeze-dried CPA product of this invention, however, is reconstituted by dissolving in water almost immediately, that is, in less than about 1 minute, and usually in less than 30 seconds. Speedy reconstitution is of great commercial significance because of the time saved by those responsible for administering the drug. The terms "dosage amount" and "product" are used herein to refer to the formulated and 'finished' CPA as it is to be presented in a dosage unit form for sale in a vial.

The sodium chloride is used to improve flow characteristics as an aid to powder filling, but it also renders the resulting reconstituted product hypertonic, which is not necessarily desirable. Moreover, the powder so obtained is relatively difficult to meter accurately into vials (as compared with the filling of an aqueous solution). Also said powder is far more difficult to prepare in terms of achieving the highly desirable pharmaceutical characteristic of homogeneity. Product cryodessicated from a homogeneous solution is, by its very nature, of optimum uniformity.

Still another problem associated with "powder-filled" vials of CPA containing NaCl (referred to herein as "stabilized CPA") is that, in common with other powders, it is difficult to exclude extraneous contaminants, particularly minute fibers and the like, which somehow find their way even into filling rooms meeting clean room standards. As a practical matter, the operation of conventional powder-filling machinery in a filling room appears to preclude an atmosphere which is free from contaminant particles. Furthermore, the generation of airborne particles of CPA powder creates a potential health hazard to the operators since CPA powder itself is a potential carcinogen.

In pharmaceutical technology, it is highly unusual to encounter a drug which can be too dry. In most cases the drier the product the more stable it is, but in the case of CPA with or without an excipient, it is found to be essential to have sufficient moisture in the product to return to the hydrate form which is essential for stability. It is generally hypothesized that this stable hydrate form is the monohydrate, but not having established this hypothesis as a fact, the rehydrated CPA is referred to herein as "CPA hydrate". By "hydrate" I refer to a compound formed by the chemical combination of water (bound) to CPA in a definite molecular ratio.

It will now be evident why freeze drying an aqueous solution of CPA with or without an excipient, and adjusted for desirable tonicity, would be a preferred manner of marketing dosage amounts of stable CPA hydrate. However, CPA hydrate, whether by itself, or with an excipient, is known to defy freeze drying so as to retain to hydrate form which is critical for stability. Further, CPA hydrate, whether by itself, or with an excipient, is known to defy freeze drying so as to yield a pharmaceutically elegant product. By "pharmaceutically elegant" I refer to a product which is visually pleasing, a criterion commonly used by those skilled in the art to gauge the market quality of the pharmaceutical. To be market quality, that is, marketable in conventional channels of the pharmaceutical trade, freeze dried CPA product must be both stable and pharmaceutically elegant.

In more qualitative terms such a pharmaceutically elegant product has a uniform appearance, and as examined from outside a glass vial or other container in which the product is held, is essentially free from bubbles or voids which individually do not exceed 2 mm in equivalent diameter ("equiv. diam."). The great difficulty associated with freeze drying a solution of CPA, whether alone, or with an excipient, is particularly noteworthy because combinations of numerous excipients, and many more drugs than excipients, are conventionally easily freeze-dried to produce elegant product.

Freeze-dried pharmaceuticals are highly preferred, because they are essentially free of particulate contaminants and are likely to have the sought-after pharmaceutical elegance. They are of better quality than equivalent powders, and can be dissolved in solvent just prior to use more easily than comparable powder filled pharmaceuticals.

The freeze drying method produces a product which is sterile and uncontaminated because it permits filtration of a solution of the desired product prior to filling. Such filtration is conventionally done through suitable microbiological filters. The procedure is far preferable to the techniques of powder filling. The filtered solution may then be precisely subdivided into suitable vials, and the vials then loaded into freeze-drying chambers where the solution is frozen and the ice sublimed under vacuum in a drying step, followed by a desorption step in which the moisture level is reduced to less than 3% by wt based on the weight of total solids, and preferably to less than 1.0% by wt.

The heretofore lack of success in freeze-drying CPA and producing an acceptable product, is particularly noteworthy because numerous drugs are routinely freeze dried to yield pharmaceutically elegant product. Drugs are often freeze-dried with sugars such as sucrose and lactose, and polyhydroxy alcohols (polyols) such as sorbitol and mannitol. For example, drugs freeze dried with mannitol include Platinol ® (Bristol-Myers), DTIC-Dome (Miles), and Dantrium IV ® (Norwich-Eaton), inter alia; those with sucrose, Palosein ® (Diagnostic Data. Inc.), inter alia; those with lactose, Aclacinomycin (National Cancer Institute), inter alia.

Numerous attempts have been made to freeze dry CPA containing sodium chloride alone, but to date, the results have been unsatisfactory. Attempts have also been made to take advantage of the superior marketability of freeze-dried CPA containing an excipient in addition to NaCl, or without it, such excipient being chosen for desirable bulking, but to date, the results have also been unsatisfactory. The product with excipient, when dried to less than 7% by wt moisture, based on the total wt of product, is unsightly. By "unsightly" I refer to a cake in which there is flaking evidenced by plate-like flakes and granular odd-sized agglomerates.

When dried in a single stage, attempting to obtain a moisture content in the right amount for stability of the CPA product, by stopping the drying of the product in the vials loaded in the chamber, fails to provide a substantially uniform moisture content in all the vials. Though some vials may contain the right amount of moisture, the moisture content of the vials in the chamber is non-uniform and difficult to control utilizing conventional drying techniques. For example, a batch of 300 vials, each containing a 100 mg dosage amount of CPA and about 75 mg of mannitol as an excipient, when freeze dried to arrive at the desired moisture content (2 to 7% by wt based on the content of the vial), produced less than 100 vials which were in the desired moisture range. Moreover, the actual moisture content of individual acceptable vials varied widely within the range. As stated hereinabove, the moisture content of the CPA product is critical because outside the critical range, the product lacks the required stability of a marketable CPA product.

When too dry, that is, when the moisture bound to the CPA as water of hydration is substantially reduced, that is to less than 5.5% by wt on an excipient-free basis, and particularly when less than 3%, the product with no excipient in it melts at room temperature. Such melting also occurs when an excipient is present and the CPA product has less than 2% by wt moisture based on the wt of the product.

When the product is too wet, that is, when the moisture bound to the CPA as water of hydration is greater than 7% by wt, the product is both pharmaceutically inelegant and unstable. Such a high moisture content is present when the moisture content of the product, including excipient(s), is greater than 7% by wt based on the total wt of product.

Whether too dry, or too wet, the CPA product includes easily visible fissures wider than 2 mm, and/or large voids within the cake greater than 2 mm and generally even greater than 3 mm in equiv. diam. Bubbles, apparently caused by puffing during freeze drying, are also formed on the surface, at least some of which are greater than 2 mm in equiv. diam. Whether either voids or bubbles are present, or both, a dosage amount of CPA containing either is deemed unsuitable for the marketplace. It is realized that such suitability may vary particularly as applied to various countries in the world, but I use the term in relation to meeting the highest standards.

Though it is generally acknowledged that the visual appearance of adequately dry CPA product do not affect its pharmaceutical efficacy, purchasers and dispensers of pharmaceuticals expect freeze dried products to have pharmaceutical elegance which otherwise dried, powder filled CPA so conspicuously lacks, and they expect to get such elegance. Most of all, they expect to get it without sacrificing the stability of the drug.

In my numerous unsuccessful previous attempts directly to freeze-dry (that is, without a rehydration step) an aqueous solution of CPA containing at least an equivalent amount by weight ("equiv wt") of an excipient, and attempts to do so with a solution containing lesser amounts, with or without NaCl, caused ice to sublime so erratically that the result was a freeze-dried CPA product characterized by flaking, granulation, fissures, 'blisters' or large bubbles referred to hereinabove, and random voids both large and small within the cake, so as to present a highly non-uniform, muddy, visually non-aesthetic appearance.

I am unaware of any disclosure relating to the freeze drying of a solution of CPA alone, or containing either NaCl or at least an equivalent weight of a sugar excipient, or both, intimately intermixed to produce a market quality, stable, freeze dried pharmaceutically elegant CPA product. By "stable" I refer to the ability of the CPA product to maintain, within specified (USP) limits of from 90% to 110% of the label potency of the freeze dried product after six months storage up until the date specified for its use, generally less than two years from the date of manufacture, at the recommended storage temperature (ambient, 20°–25° C.) when subjected to conditions defined in the USP procedure for high pressure liquid chromatographic ("HPLC") testing. The effectiveness of the drug is predicated upon its purity as active drug substance, that is, freedom from unacceptable degradation.

Except for the sugars disclosed herein, I found no other excipients which by themselves produced a market quality freeze dried CPA product. For the purposes herein, NaCl is not an excipient. Its presence in the freeze-dried CPA product is unnecessary. NaCl may be added in a minor amount by wt relative to the CPA (anhyd) to adjust the tonicity of the reconstituted CPA solution. The presence of a buffer salt is generally also unnecessary but a minor amount by wt relative to the CPA (anhyd) may be added to ensure that the pH of the reconstituted solution is in the desired range of from about 3.5 to about 5.5.

I have been unable to freeze-dry CPA monohydrate product without an excipient, with or without NaCl. Even disaccharides by themselves are not particularly desirable from the point of view of producing a pharmaceutically elegant product, because they can exhibit erratic lyophilization characteristics and may be reconstituted with difficulty for use as aqueous solutions. Polyols such as mannitol, galactitol and sorbitol are incorporated with difficulty into acceptably freeze-dried CPA product unless the mannitol is present in an equiv. wt, or, a major amount by wt of the sugars including polyols used as excipients, the equivalent or minor amount being anhydrous CPA. For the purpose herein, aldoses, ketoses and polyols used as excipients are collectively referred to herein as sugars.

SUMMARY OF THE INVENTION

It has been discovered that an aqueous solution of cyclophosphamide ("CPA") with at least one-half as much by weight of mannitol as an excipient, (that is, at least 0.5 times the equivalent weight of anhydrous CPA is mannitol), when freeze-dried to a moisture content below 2% by wt, based on the net content of a vial containing the freeze-dried material, can be rehydrated or remoisturized to a desired moisture content of from 2 to 7% by wt based on the net content, so as to yield a pharmaceutically elegant product which is stable; the CPA product is obtained more reliably than if the solution is directly freeze-dried to the desired moisture content, that is, without a rehydration step.

A two-stage process has been discovered for producing a dosage amount of stable CPA hydrate together with at least half as much as (0.5 times), and preferably from about 1.25 to 5 times as much, of mannitol present as an excipient in a major amount by wt relative to CPA (anhyd), as a lyophilized (hereafter "freeze-dried") product which is pharmaceutically elegant and in which it is critical that the integrity of the CPA hydrate is maintained. The bulk density of the CPA product is in the range from 0.05 g/cc to 0.2 g/cc and the moisture bound to the CPA hydrate is in the range from 5% to 7% based on the wt of CPA hydrate. This is obtained when the moisture content of the CPA product is in the range from 2% to 7% by wt based on the total net content wt of the product.

It is therefore a general object of this invention to provide a process for freeze drying a solution of CPA, comprising, in a first stage, (a) freezing an aqueous solution of a dosage amount of CPA and at least half as much as (0.5 times) an equiv wt of a sugar, by cooling and freezing the solution to a temperature in the range from about −25° C. to about −50° C. as determined by probes in vials racked in a tray placed on a shelf of a freeze-drying chamber; (b) maintaining vacuum control for an extended period of time after the temperature of the material in the vials is in the range from above about −50° C. to about 25° C. so that the moisture content of the freeze-dried material formed in the vials is less than about 2% based on the total net content wt of the freeze dried material; and, in a second stage, (c) rehydrating (or remoisturizing) the freeze-dried material by (i) introducing water vapor directly into the chamber until it reaches about 75% relative humidity or higher, and (ii) maintaining the humidity at this level for a period of time sufficient to permit the freeze-dried material to attain a moisture content in the range from 2% to 7% by wt, based on the net content wt of the CPA product.

It is also a general object of this invention to provide a novel freeze-dried CPA product in a dosage amount which is pharmaceutically elegant and stable, and which contains at least an equiv wt of mannitol relative to CPA (anhyd), and optionally another sugar, buffer salt, or carboxylic acid, provided the combined weight of the carboxylic acid, buffer salt and sodium chloride, if present, is less than the weight of the sugar(s).

DETAILED DESCRIPTION OF PREFERRED EMBODIMENTS

Conventional freeze-drying of an aqueous solution of cyclophosphamide with an excipient selected from the group consisting of monosaccharides and disaccharides results in CPA product of unacceptable market quality because it has non-uniform CPA hydrate integrity and poor shelf-life stability. By "hydrate integrity" I refer to the bound moisture content of the CPA hydrate being sufficient to provide stability of the product, which content is hypothesized to be in the range from 5% to 7% by wt of the CPA hydrate; and, by "uniform" I refer to substantially all vials in a batch of at least several hundred vials being freeze dried to within a moisture range of from 2% to 7% by wt based on the net wt of product in a vial. The criticality of maintaining the CPA hydrate integrity is premised on the knowledge that the moisture content of the CPA product cannot exceed 7% by wt, and the particular proportioning of this moisture relative to each component of the product is not narrowly critical.

Such conventional freeze-drying typically includes the following steps: (a) freezing the solution to a temperature in the range from about −10° C. to about −45° C. in a vial; (b) evacuating the freeze-drying chamber to a pressure lower than about 1000 micrometers and holding the frozen solution at reduced pressure for a period of about 6 hours; and (c) raising the shelf temperature incrementally to about 25° C. over a period of about 60 hours until the moisture content of the cake in the vial is in the range from 5% to 7% by wt based on the CPA hydrate content of the product. For those who were unaware of the criticality of maintaining the integrity of the CPA hydrate, step (c) was carried out until the moisture content of the vial was 2% by wt or lower, based on the total wt of product. The chamber is then bled to a predetermined pressure and the vials are capped.

In practice, a large number of vials of solution, each vial containing a dosage amount of CPA, are racked upright in a tray, adjacent to each other so as to form an assembly which may be capped with stoppers when the freeze-drying cycle is completed. This is conveniently effected with available apparatus, for example such as is disclosed in U.S. Pat. No. 3,286,366.

The CPA product produced by prior art freeze drying processes is unsightly, thus visually unacceptable from a marketing point of view, though it may or may not be pharmaceutically less active than the CPA product of my invention. The poor visual quality of the prior art product is in part due to a tough skin, attributable to an inappropriate choice of excipient, and inadequate control of the freeze-drying cycle. The skin formed on the product interferes with evaporative cooling, the temperature of the interior of the product rises, and the product flakes, granulates, "puffs" and splits. The rise in temperature may be sufficient to melt the product forming a visually distinct phase, and upon cooling, the product collapses, shrinks away from the walls of the vial, and allows fissures, voids and bubbles to form within and upon the product. These defects are readily perceived by observation through the walls of a glass vial with the naked eye, so that products produced by conventional freeze-drying processes are deemed not to be pharmaceutically elegant.

By a "dosage amount" of CPA I refer to a specified amount of pure CPA (anhydrous) which may, if desired, include a 5% overage, and one or more excipients optionally with NaCl. Typically, dosage amounts of my invention are 100 mg, 200 mg, 500 mg, 1 g and 2 g of CPA anhydrous, not including an overage, and contain as an excipient at least an equivalent amount by weight ("equiv. wt.") of mannitol, and up to 5 times by wt of the mannitol. Where more than one sugar is used, at least an equiv wt of CPA (anhyd) is mannitol, and all or part of the remaining amount by wt of excipient may be another sugar, for example, lactose. A typical powder filled basic dosage ("B.D.") amount is 500 mg CPA anhydrous (that is, about 535 mg of CPA monohydrate) with 225 mg of NaCl in a 30 ml vial, and when reconstituted, forms a CPA solution having a pH in the range from about 3.5 to about 7, and is hypertonic. Another dosage amount is double the "B.D." amount and being twice as large, is packaged in a 60 ml vial. Other dosage amounts which are multiples, including fractions, of the B.D. amount may also be prepared, with or without NaCl.

In one preferred embodiment, the product of my invention is a freeze-dried CPA product which contains a sugar, such as a polyol having from 5 to about 9 carbon atoms, and particularly mannitol, sorbitol and galactitol; or, a monosaccharide such as an aldose having from 5 to about 10 carbon atoms, preferably the naturally occurring aldohexoses such as glucose (dextrose), mannose, galactose, and the like; or, a disaccharide having 12 carbon atoms, particularly the naturally occurring sucrose and lactose; or, a polysaccharide such as starch. The combination of excipients may include any of the foregoing, and a carboxylic acid such as succinic acid, citric acid and maleic acid; and a buffer salt such as an acetate, citrate, bicarbonate, phosphate, or the like of sodium or potassium; but, in any combination of excipients, the weight of the sugar(s) present must be greater than the weight of the remaining excipients, if these are present. Further, particularly where an isotonic reconstituted solution is desired, the amount of the sugar present is necessarily at least equivalent in weight to the amount of the CPA in solution.

In the most preferred embodiment and best mode, the only excipient is mannitol present in an amount from about 1.25 times to about 5 times the weight of CPA in the product. Even greater amounts of mannitol may be used without adversely affecting the market quality or potency of the CPA product but "loading" the product, with mannitol serves no particularly useful purpose in this case.

The CPA product is formed in a wide range of thicknesses of from about 0.1 mm to about 5 cm, but preferably in the range from about 5 mm to about 3 cm thick. The B.D. amount is most preferably formed in a thickness in the range from about 1 cm to about 1.5 cm thick. The product has a uniform, near-white color and is essentially free of flaking or granular agglomerates.

Irrespective of the thickness of the product, the bulk density of the freeze-dried product is in the range from about 0.05 g/cc to about 0.2 g/cc. The bulk density of the dried CPA product depends upon the concentration of the excipient(s) in the solution from which the product is derived, whether the product contains NaCl, and the particular conditions of freeze drying.

The product is free from unsightly flakes, granules or bubbles on its surface, or voids which are greater than about 2 mm in equiv. diam., or fissures (freezing-cracks) which are wider than 2 mm. Since typically, voids within a product are of unpredictable size and shape, their dimensions are stated in equivalent diameters. It will be recognized that a product having a depth of 1 mm may have included therewith a disc-shaped void which has an equiv. diam. of 2 mm or more. Similarly, the product having a thickness of about 1 mm may have one or more bubbles on or near its surface, the shape of which bubble is longitudinal having a length greater than 2 mm but the cross-section of which varies widely in a range below 2 mm, and the size of the bubble will be over 2 mm equiv. diam.

The freeze-dried CPA product of this invention, most preferably has minute bubbles, voids and fissures which are barely discernible to the naked eye, if at all. By "freeze-dried CPA product" I refer to product in which the integrity of the CPA hydrate is maintained, that is, having a bound moisture content of from about 5% to about 7% by wt based on CPA hydrate content, and most preferably from about 5.8% to about 6.7%. Since the moisture content of the CPA hydrate, apart from the moisture content of the excipient(s), is difficult to measure, it is convenient to state that this requirement is met when the product has a moisture content in the range from 2% to 7% by wt based on the total weight of formulated product. Such a product provides the requisite shelf-life stability which is evidence that the integrity of the CPA hydrate is maintained. Moisture determination is made by any standard method, as for example, described in Edwards supra, the Karl Fischer procedure being preferred.

The size of the vial chosen is determined by the dosage amount, the B.D. amount (500 mg of CPA) being provided in B.D. vials ranging from 20 ml to 50 ml, and most preferably 25 or 30 ml. Most preferred for a B.D. amount is a 30 ml vial in which 15 ml of solution contains 500 mg of CPA (anhyd), about 1 g of mannitol, and a quantity of water sufficient (QS) to bring the volume to 15 ml. Since the volume of the freeze-dried and rehydrated CPA product does not change substantially from the initial volume of the solution in the vial, the bulk density is about 0.1 g/cc. Bulk density increases for the same dosage amount but increases with increasing amounts of excipient if the solution volume does not change.

Precisely how the freeze drying cycle is monitored is not critical and this may be effected in various ways, for example as suggested in *Freeze Drying Processes for the Food Industry*, by Gutcho, M. H., published by Noyes Data Corporation, N.J. (1977). The essential elements in the cycle are the monitoring of the temperature of the shelves, the temperature of the material in the vials, and the time periods during which the temperature and pressure conditions are controlled.

The chamber is evacuated after the vials are frozen and a temperature from about $-20°$ C. to about $-50°$ C. is maintained for enough time to ensure that all the vials are at substantially the same temperature. A higher temperature may be used if time is not a factor, but temperatures much warmer than $-20°$ C. are not economical. A pressure of no more than 1000 micrometers is essential, and it is preferred to use a pressure in the range from about 10-500 micrometers which may be effected with any conventional high quality vacuum pump. The time during which the chamber is evacuated is not critical as long as the material in the vials is frozen solid, a typical evacuation period ranging from about 10 mins to about 1 hr.

The shelf temperature is raised gradually, the rate being controlled by a control means such as a cam, or microprocessor, or by manual control, so that the shelf temperature reaches a finish-drying temperature no higher than that which deleteriously affects the CPA material. Too high a temperature causes the material to melt or otherwise be degraded, adversely affecting both its pharmaceutical efficacy and elegance.

The vacuum is maintained throughout the drying cycle, and in all cases should be sufficient to produce dried material with a moisture content of less than 2% by wt based on total net content wt of the dried material. The period of time will depend upon the dosage amounts in the vials, the size and configuration of the vials, and the number of vials in an assembly in the particular chamber being used.

After the vials have been dried to the aforespecified degree in the first stage of the process, the freeze-dried material is rehydrated by introducing water vapor into the chamber. A fine spray of water may be jetted intermittently into the chamber in an amount sufficient to raise the moisture level in the chamber above 75% relative humidity. Any source of pure water may be used, but clean steam is preferred because it is convenient and lends itself to precise control. Sufficient clean steam is introduced over a period of time in the range from about 5 min to about 2 hr, to attain a relative humidity of about 85% in the chamber, and the humidity is maintained at this level until it is determined that the material in the vials has absorbed enough moisture to meet the preferred range of from about 5.8% to about 6.7% by wt based on the CPA monohydrate content of the product, or from 2% to 7% by wt based on the total net content wt of product.

In an analogous manner, the process may be carried out in vials in which a dosage amount includes less than an equivalent wt of the excipient. For pharmaceutical elegance and stability it is preferred that the wt of excipient be at least one half the wt of active drug substance. Dosage amounts with less than an equivalent wt of mannitol are hypotonic.

EXAMPLE

The best mode for practicing the invention for the preparation of a 500 mg dosage amount of CPA as the hydrate with an excipient is as follows:

Bulk CPA stated to be a white crystalline powder on the supplier's certificate of analysis (100% CPA) of CPA monohydrate is analyzed for moisture. The analysis indicates a moisture content of about 7%. A bulk solution of CPA in Water for Injection, USP is made up containing about twice as much mannitol as CPA (anhyd) by wt, the mannitol being preferably added after the CPA is dissolved in about 85% of the QS volume of water, the QS volume being the volume of water required (quantity sufficient) to make up the desired solution volume in all the vials. Solution of the mannitol is assisted by vigorous mixing. This solution is brought up to QS volume, clarified through a 10 micrometer filter, and sterilized by flowing it through a 0.2 micrometer sterile filter, for example, a NR66 nylon Ultipore made by Pall Trinity Corp.

This filtered 'QS solution' is metered into a large number of 30 ml glass vials so that each of several thousand vials contains 535 mg of CPA monohydrate (with no overage) and 950 mg of mannitol, the volume of solution in each vial being approximately 15 ml. If desired, an overage may be added for specified shelf-life and vial-needle-syringe (VNS) retention. A buffer salt may be added to maintain the desired pH in the range from 3 to 6, more preferably from about 3.9 to 4.5.

The vials, some with thermocouple probes in them, are racked in trays and placed on the shelves of a suitable freeze drying chamber.

In the first stage of freeze drying, the product solution in the vials is frozen to a temperature of $-20°$ C. or lower, and after all the probes give the desired temperature, this temperature is maintained for about 2 hr. The condenser is chilled to $-50°$ C. or below and the chamber is evacuated, the vacuum being adjusted with a $N_2$ sweep to read in the range from about 10-1000 micrometers. The shelves are then warmed to about $+22°$ C. and when the probes in the vials read about $+20°$ C., the vacuum is maintained for about 4 to 24 hr without exceeding about 25° C. for any significant period of time.

In the second stage, rehydration of the freeze dried material is accomplished by introducing water vapor directly into the chamber until it reaches about 85% relative humidity, the water preferably being in the form of clean steam passed through a sterile microbiological filter. When the chamber has reached an equilibrium value of about 80% to about 85% relative humidity, this humidity is maintained until the product acquires a moisture content in the range from 2% to 7% by wt based on the total wt of the formulated product. The moisture level is monitored periodically by removing representative samples (vials) in a lot and carrying out a Karl Fischer analysis. The relative humidity of the chamber for rehydration is not critical, it being evident that rehydration will take place when the vapor pressure in the chamber is greater than that of the freeze-dried material. Thus, the freeze-dried material is rehydrated by (i) exposing the material to a moist atmosphere having a relative humidity of at least 75%, and (ii) maintaining the relative humidity at this level for a period of time sufficient to permit the material to attain a moisture content in the range from 2% to 7% by wt, based on the net wt of CPA product. It is preferred that the humidity of the chamber be 80–85% because at lower humidity the rehydration is impractical.

Rehydration of the freeze dried material obtained after the first stage may also be effected as follows:

A. The vials of freeze dried material are removed from the freeze drying chamber and placed in a constant humidity cabinet for rehydrating the material. The material is held in the constant humidity cabinet until it is determined that the material in the vials has absorbed enough moisture to meet the critical moisture content of CPA product. The vials of rehydrated CPA product are then removed from the constant humidity cabinet and stoppered.

B. The vials of freeze dried material are placed in a chamber over a constant humidity solution with a humidity value of 80–90%. The material is held in the chamber over the solution until it is determined that the material has absorbed enough moisture to meet the specification of the critical moisture content of CPA product. At the end of the rehydration step, the chamber is restored to a predetermined pressure and the vials are stoppered.

The freeze dried cake formed has pharmaceutical elegance, and excellent stability as required by the standards set for dosage amounts of CPA.

In a manner analogous to that described in the foregoing example several batches of CPA product were freeze-dried in various dosage amounts with mannitol as the only excipient, and more than 100 vials from each batch were placed on a stability test in a controlled atmosphere room at an ambient temperature of 20°–25° C. Samples of vials (3 for each test interval) were taken at random from each batch and analyzed at the intervals indicated, and the results recorded in the following Table. The assays were made according to the procedure described in the USP monograph HPLC method. The variation in assay is within the specified range of 90–100% CPA set forth in the USP monograph. Degradation indicating a lack of adequate stability would be evidenced by a significantly lower assay (considering experimental error) at the end of a test period, than the initial assay. As will be evident from the representative tests set fort below, there is no evidence of degradation at the end of six months. Assays made at the end of 1 month, and at the end of 3 months, are not given.

I claim:
1. A two-stage process for freeze-drying cyclophosphamide ("CPA") hydrate, comprising, in a first stage,
  (a) freezing an aqueous solution of a dosage amount of CPA and an excipient selected from the group consisting of a polyhydroxy alcohol having from 5 to about 9 carbon atoms, a monosaccharide having from 5 to about 10 carbon atoms, a disaccharide and a polysaccharide, provided said excipient is present in an amount at least 0.5 times the equivalent weight ("equiv wt") of anhydrous CPA, by cooling and freezing the solution to a temperature in the range from about −20° C. to about −50° C.;
  (b) maintaining vacuum control after the temperature of the product is in the range from above about −50° C. to about 25° C. until the moisture content of the freeze-dried material is less than about 2% based on the total net wt of CPA product; and, in a second stage;
  (c) rehydrating the freeze-dried material by (i) contacting the freeze-dried material with live steam until the relative humidity to which the material is exposed is about 80–85%, and (ii) maintaining the relative humidity at this level such that the material attains a moisture content in the range from 2% to 7% by wt, based on the net wt of CPA product, so as to maintain the integrity of said CPA hydrate; whereby a cake of CPA hydrate and excipient having uniform appearance and consistency is produced.

2. The process of claim 1 wherein in step (c) (ii) the bound moisture content of said CPA hydrate is in the range from about 5% to about 7% by wt of CPA hydrate.

3. The process of claim 2 wherein said polyhydroxy alcohol is selected from mannitol, sorbitol and galactitol, said monosaccharide is an aldohexose, said polysaccharide is starch and said carboxylic acid is selected from maleic acid, citric acid and succinic acid.

4. The process of claim 1 wherein said polyhydroxy alcohol is present in a major proportion by wt relative to the disaccharide when both are present.

5. The process of claim 2 wherein said excipient is present in an amount in the range from about 1.25 to about 5 times the wt of the CPA (anhydrous).

6. The process of claim 3 wherein only said polyhydroxy alcohol is present in an amount in the range from about 1.25 times to about 5 times the weight of the CPA (anhydrous).

7. The process of claim 6 wherein mannitol is the only polyhydroxy alcohol present in an amount in the range from about 1.25 times to 5 times the wt of CPA (anhydrous).

8. The process of claim 7 wherein mannitol is present in an amount in the range from about 1.25 times to about 2 times the wt of CPA (anhydrous), and there is also

TABLE

| Dosage amt. (g) | Initial | | | | after 6 months | | | |
|---|---|---|---|---|---|---|---|---|
| | assay (HPLC) % | pH | moisture K. Fischer % | reconstit'n time min | assay (HPLC) % | pH | moisture K. Fischer % | reconstit'n time min |
| BV-CI(0.1)-1A | 101.0 | 4.27 | 4.16 | 0.5 | 101.7 | 4.22 | 2.55 | 0.5 |
| BV-CI(0.2)-1A | 97.6 | 4.31 | 3.69 | 0.5 | 103.7 | 4.32 | 2.75 | 0.5 |
| BV-CI(0.5)-1A | 99.9 | 4.11 | 3.67 | 1.0 | 100.4 | 4.03 | 2.90 | 1.0 |
| BV-CI(1.0)-1A | 100.2 | 4.08 | 3.61 | 1.0 | 102.0 | 4.27 | 3.19 | 1.5 |
| BV-CI(1.0)-1A | 101.2 | 4.00 | 2.87 | 1.0 | 102.4 | 4.30 | 3.17 | 2.0 | present a minor amount of NaCl compared to the wt of the CPA (anhydrous).

9. In a process for freeze drying a dosage amount of cyclophosphamide ("CPA") hydrate from an aqueous solution, the improvement comprising carrying out said process in two stages, the first stage comprising freeze drying a solution of CPA hydrate in combination with from about 0.5 times to about 5 times its weight ("wt") of an excipient in which mannitol is present as the major excipient by wt, until the moisture content of freeze-dried material is less than 2% by wt based on the wt of CPA hydrate in the freeze-dried material, and the second stage comprising rehydrating the freeze-dried material by contacting it with live steam until the relative humidity to which the material is exposed is about 80–85% and maintaining the relative humidity at this level so that the moisture content of the product is in the range from about 2% to 7% based on the total net wt of CPA product, and the integrity of said CPA hydrate is maintained.

10. The process of claim 9 wherein the bound moisture content of said CPA hydrate is in the range from about 5% to about 7% by wt based on the wt of CPA hydrate.

11. The process of claim 1 wherein a carboxylic acid or buffer salt is also present in said aqueous solution.

12. The process of claim 11 wherein said polyhydroxy alcohol is selected from mannitol, sorbitol and galactitol, said monosaccharide is an aldohexose, said polysaccharide is starch and said carboxylic acid is selected from maleic acid, citric acid and succinic acid.

13. The process of claim 11 wherein said polyhydroxy alcohol is present in a major proportion by wt relative to the disaccharide when both are present.

14. The process of claim 11 wherein in step (c) (ii) the bound moisture content of said CPA hydrate is in the range from about 5% to about 7% by wt of CPA hydrate.

15. The process of claim 14 wherein said excipient is present in an amount in the range from about 1.25 to about 5 times the wt of the CPA (anhydrous).

16. The process of claim 1 wherein said relative humidity in step (c) (ii) is maintained for at least 5 minutes so that the material attains a bound moisture content of CPA in the range from 5.8% to about 6.7% by wt. based on the wt of CPA hydrate.

17. The process of claim 12 wherein only said polyhydroxy alcohol is present in an amount in the range from about 1.25 times to about 5 times the weight of the CPA (anhydrous).

18. The process of claim 17 wherein mannitol is the only polyhydroxy alcohol present in an amount in the range from about 1.25 times to 5 times the wt of CPA (anhydrous).

19. The process of claim 18 wherein mannitol is present in an amount in the range from about 1.25 times to about 2 times the wt of CPA (anhydrous), and there is also present a minor amount of NaCl compared to the wt of the CPA (anhydrous).

20. The process of claim 13 wherein a minor amount of NaCl relative to the weight of said CPA (anhydrous) is present.

21. The process of claim 4 wherein a minor amount of NaCl relative to the weight of said CPA (anhydrous) is present.

* * * * *